United States Patent [19]
Masters et al.

[11] Patent Number: 5,919,682
[45] Date of Patent: *Jul. 6, 1999

[54] OVERPRODUCTION OF NEURONAL NITRIC OXIDE SYNTHASE

[75] Inventors: Bettie Sue Masters; Linda J. Roman, both of San Antonio, Tex.; Essam A. Sheta, Bolkly, Egypt

[73] Assignee: Board of Regents, University of Texas System, Austin, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/519,105

[22] Filed: Aug. 24, 1995

[51] Int. Cl.$^6$ .............................. C12N 9/02; C12N 15/53; C12N 15/70
[52] U.S. Cl. ................... 435/189; 435/69.1; 435/252.3; 435/252.33; 536/23.2
[58] Field of Search .................................. 435/69.1, 183, 435/189, 252.3, 252.33, 25.33

[56] References Cited

U.S. PATENT DOCUMENTS

| | | | |
|---|---|---|---|
| 5,240,831 | 8/1993 | Barnes | 435/69.1 |
| 5,268,465 | 12/1993 | Bredt et al. | 435/252 |

OTHER PUBLICATIONS

Makrides, 60(3) Microbiol. Rev. 512–538 (1996).
Lee et al., 267(5) J. Biol. Chem. 2849–52 (1992).
Studier et al., 185 Meth. Enz. 60–89 (1990).
Barnes et al., "Expression and enzymatic activity of recombinant P450 17α–hydroxylas in *Escherichia coli*", *Proc. Natl. Acad. Sci. USA*, 88:5597–5601, Jul. 1991.
Bredt et al., "Cloned and expressed nitric oxide synthase structurally resembles cytochrome P–450 reductase", *Nature*, 351:714–718, Jun. 1991.
Bredt, David S. and Solomon H. Snyder, "Isolation of nitric oxide synthetase, a calmodulin–requiring enzyme", *Proc. Natl. Acad. Sci. USA*, 87:682–685, Jan. 1990.
Bredt, D.S. and S.H. Snyder, "Nitric Oxide: A Physiologic Messenger Molecule", *Ann. Rev. Biochem.*, 63:175–195, 1994.
Busconi, Liliana and Thomas Michel, "Recombinant Endothelial Nitric Oxide Synthase: Post–translational Modifications in a Baculovirus Expression System", *Molecular Pharmacology*, 47:655–659, 1995.
Charles et al., "Cloning and Expression of a Rat Neuronal Nitric Oxide Synthase Coding Sequence in a Baculovirus/Insect Cell System", *Biochemical and Biophysical Research Communications*, 196(3):1481–1489, Nov. 1993.
Cho et al., "Calmodulin Is a Subunit of Nitric Oxide Synthase from Macrophages", *J. Exp. Med*, 176:599–604, Aug. 1992.

(List continued on next page.)

*Primary Examiner*—Robert A. Wax
*Assistant Examiner*—William W. Moore
*Attorney, Agent, or Firm*—Arnold White & Durkee

[57] ABSTRACT

The present invention is directed to overproduction of nitric oxide synthase (NOS) in a prokaryote. More particularly, the invention involves overexpression of functional neuronal NOS in a protease-deficient strain of *Escherichia coli*, utilizing a pCW vector under the control of the tac promotor. The invention further involves co-expression of the protein with folding agonists, or chaperonins. The enzyme produced is complete with heme and flavins, and may be activated by incubation with tetrahydrobiopterin. It may be isolated as a predominantly high spin heme protein that demonstrates spectral properties which are identical to those of nNOS isolated from human kidney 293 cells. The methods disclosed are contemplated to be useful in expressing large amounts of other nitric oxide synthases, as well as other proteins that are difficult to produce correctly folded in prokaryotes.

4 Claims, 7 Drawing Sheets

OTHER PUBLICATIONS

Förstermann et al., "Calmodulin–dependent endothelium–derived relaxing factor/nitric oxide synthase activity is present in the particulate and cytosolic fractions of bovine aortic endothelial cells", *Proc. Natl. Acad. Sci. USA*, 88:1788–1792, Mar. 1991.

Fukushima, Takeshi and Jon C. Nixon, "Analysis of Reduced Forms of Biopterin in Biological Tissues and fluids", *Analytical Biochemistry*, 102:176–188, 1980.

Fukuto, J.M. and G. Chaudhuri, "Inhibition of Constitutive and Inducible Nitric Oxide Synthase: Potential Selective Inhibition", *Annu. Rev. Pharmacoi Toxical*, 35:165–194, 1995.

Gegner, Julie A. and Frederick W. Dahlquist, "Signal transduction in bacteria: CheW forms a reversible complex with the protein kinase CheA", *Proc. Natl. Acad. Sci. USA*, 88:750–754, Feb. 1991.

Geller et al., "Molecular Cloning and Expression of Inducible Nitric Oxide Synthase From Human Hepatocytes", *Proc. Natl. Acad. Sci USA*, 90:3491–3495, Apr. 1993.

Gerber, N.C. and P.R. Ortiz de Montellano, "Active Site Topology of Nitric Oxide Synthase Expressed in *E. Coli*", *FASEB J.* 9, A1490 (Abstract #1552).

Gerber, N.C. and P.R. Ortiz de Montellano, "Neuronal Nitrate Oxide Synthase, Expression in *Escherichia coli*, Irreversible Inhibition by Phenylidiazene, and Active Site Topology", *The Journal of Biological Chemistry*, 270(30):17791–17796, Jul. 1995.

Goloubinoff et al., GroE heat–shock proteins promote assembly of foreign prokaryotic ribulose bisphosphate carboxylase oligomers in *Escherichia coli*, 337:44–47.

Gross, Steven S. and Roberto Levi, "An Absolute Requirement for Cytokine–Induced Nitric Oxide Generation by Vascular Smooth Muscle", *The Journal of Biological Chemistry*, 267(36)25722–25729.

Hevel et al., Purification of the Inducible Murine Macrophage Nitric Oxide Synthase, *The Journal of Biological Chemistry*, 266(34):22789–22791.

Janssens et al., "Cloning and Expression of a cDNA Encoding Human Endothelium–Derived Relaxing Factor/Nitric Oxide Synthase", *The Journal of Biological Chemistry*, 267(21):14519–14522, 1992.

Kelm, Malte and Jügen Schrader, "Control of Coronary Vascular Tone by Nitric Oxide", *Circulation Research*, 66(6):1561–1575, Jun. 1990.

Kim et al., "Cystosolic chaperonin subunits have a conserved ATPase domain but diverged polypeptide–binding domains", *TIBS 19*, 1543–548, Dec. 1994.

Klatt et al., "Brain nitric oxide synthase is a haemoprotein", *Biochem J.*, 288:15–17, 1992.

Kobzik et al., "Nitric Oxide in Skeletal Muscle", *Nature*, 372:546–548, Dec. 1994.

Lamas et al., "Endothelial nitric oxide synthase: Molecular cloning and characterization of a distinct constitutive enzyme isoform", *Proc. Natl. Acad. Sci. USA*, 89:6348–6352, Jul. 1992.

Lowenstein et al., "Cloned and expressed macrophage nitric oxide synthase contrasts with the brain enzyme", *Proc. Natl. Acad. Sci. USA*, 89:6711–6715.

Michael A. Marletta, "Nitric Oxide Synthase Structure and Mechanism", *The Journal of Biological Chemistry*, 268(17):12231–12234, 1993.

Martinus et al., "Role of chaperones in the biogenesis and maintenance of the mitochondrion", *The FASEB Journal*, 9:371–378.

Bettie Sue Siler Masters, "Nitric Oxide Synthases: Why So Complex"? *Annu. Rev. Nutr.*, 14:131–145, 1994.

Mayer et al., "Brain nitric oxide synthase is a biopterin– and flavin–containing multi–functional oxido–reductase", *FEBS Letters*, 288(1,2):187–191, Aug. 1991.

McMillan et al., "Cloned, expressed rat cerebellar nitric oxide synthase contains stoichiometric amounts of heme, which binds carbon monoxide", *Proc. Natl. Acad. Sci. USA*, 89:11141–11145, Dec. 1992.

McMillian et al., "Prokaryotic Expression of the Heme– and Flavin–Binding Domains of Rat Neuronal Nitric Oxide Synthase as Distinct Polypeptides: Identification of the Heme–Binding Proximal Thiolate Ligand as Cysteine–415", *Biochemistry*, 34:3686–3693, 1995.

McMillan, Kirk and Bettie Sue Siler Masters, "Optical Difference Spectrophotometry as a Probe of Rat Brain Nitric Oxide Synthase Heme–Substrate Interaction", *The American Chemical Society*, 32(38):9875–9880, Sep., 1993.

Nakane et al., "Cloned Human Brain Oxide Synthase is Highly Expressed in Skeletal Muscle", *Federation of European Biochemical Societies*, 316(2):175–180, Jan. 1993.

Nelson et al., "The P450 Superfamily: Update on New Sequences, Gene Mapping, Acession Numbers, Early Trivial Names of Enzymes, and Nomenclature", *DNA and Cell Biology*, 12(1):1–51, 1993.

Ogden J.E. and P.K. Moore, "Inhibition of Nitric Oxide Synthase—Potential for a Novel Class of Therapeutic Agent"? *TBTECH*, 13:70–78, Feb. 1995.

Pollock et al., Purification and characerization of particulate endothelium–derived relaxing factor synthase from cultured and native bovine aortic endothelial cells, *Proc. Natl. Acad. Sci. USA*, 88:10480–10484, Dec. 1991.

Richards M.K. and M.A. Marletta, "Characterization of Neuronal Nitric Oxide Synthase and a C415H Mutant, Purified from a Baculovirus Overexpression System", *Biochemistry*, 33:14723–14732, 1994.

J. S. Rieske, The Quantitative Determination of Mitochondrial Hemoproteins, *Methods Enzymol.*, 10:488–493, 1967.

Riveros–Moreno et al., "Purification to homogeneity and characerization of rat brain recombinant nitric oxide synthase", *Eur. J. Biochem.*, 230:52–57, 1995.

$Ca^{2+}$/Calmodulin–Dependent NO Synthase Type I: A Bioteroflavoprotein with $Ca^{2+}$/Calmodulin–independent Diaphorase and Reductase Activities, *Biochemistry*, 31(12):3243–3249, 1992.

Schmidt et al., "Purification of a soluble isoform of guanylyl cyclase–activating–factor synthase", *Proc. Natl. Acad. Sci. USA*, 88:365–369, Jan. 1991.

Seo et al., "Heme Requirement for Production of Active Endothelial Nitric Oxide Synthase in Baculovirus–Infected Insect Cells", *Biochemical and Biophysical Research Communications*, 208(1):10–18, Mar. 1995.

Sessa et al., "Molecular cloning and Expression of a cDNA Encoding Endothelial Cell Nitric Oxide Synthase", *The Journal of Biological Chemistry*, 22:15274–15276, 1992.

Sheta et al., "Evidence for a Biodomain Structure of Constitutive Cerebellar Nitric Oxide Synthase", *The Journal of Biological Chemistry*, 269(21):15147–15153, May 1994.

Solomon H. Snyder, "More Jobs for That Molecule", *Nature*, 372(8):504–505, Dec. 1994.

Stuehr et al., "Purification and characterization of the cytokine–induced macrophage nitric oxide synthase: An FAD– and FMN–containing flavoprotein", *Proc. Natl. Acad. Sci. USA*, 88:7773–7777, Sep. 1991.

Stuehr, Dennis J. and Masao Ikeda–Saito, "Spectral Characterization of Brain and Macrophage Nitric Oxide Synthases", *The Journal of Biological Chemistry*, 267(29):20547–20550, Oct., 1992.

White, Kimberly A. and Michael A. Marletta, "Nitric Oxide Synthase Is a Cytochrome P–450 Type Hemoprotein", *Biochemistry*, 31(29):6627–6631, Jul. 1992.

Wolff et al., "Calmodulin–dependent Nitric–oxide Synthase", *The Journal of Biological Chemistry*, 268(13):9425–9429, May 1993.

Wynn et al., In Vitro Reconstitution of the 24–meric E2 Inner Core of Bovine Mitochondrial Branched–chain α–Keto Acid Dehydrogenase Complex: Requirement for Chaperonins GroEL and GroES, *Biochemistry*, 33(30):8962–8968, 1994.

Xie et al., "Cloning and Characterization of Inducible Nitric Oxide Synthase form Mouse Macrophages", *Science*, 256:225–228, Apr. 1992.

Zhang, J. and S.H. Snyder, "Nitric Oxide in the Nervous System", *Annu. Rev. Pharmacoi Toxicol*, 35:213–233, 1995.

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (xi) SEQUENCE DESCRIPTION: SEQ ID NO:1:

TCATCATCAT ATAACTGAAG AGAACACGTT                    30

(2) INFORMATION FOR SEQ ID NO:2:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO:2:

CATGCTTGGC GCCAT                                    15

OVERPRODUCTION OF NEURONAL NITRIC OXIDE SYNTHASE

The government owns certain rights in the present invention pursuant to grant number HL30050 from the National Institutes of Health.

BACKGROUND OF THE INVENTION

1. Field of the Invention

The present invention relates generally to the fields of molecular biology and protein synthesis. More particularly, it concerns methods of increasing production of biologically functional nitric oxide synthase and other proteins that require specific post-translational alteration for activity.

2. Description of the Related Art

Nitric oxide synthase (NOS) catalyzes the formation of NO. and L-citrulline from L-arginine through a series of oxidations using molecular oxygen (Bredt and Snyder, 1990). There are at least three separate genes encoding the NOS family of proteins, including the constitutively expressed neuronal (nNOS) (Bredt et al.. 1991) and endothelial (ecNOS) (Lamas et al., 1992; Sessa et al., 1992) isoforms, and the inducible isoform (iNOS) (Xie et al., 1992; Lowenstein et al., 1992).

The three isoforms differ in primary sequence (having only 50–60% sequence identity), size, intracellular location, and regulation. Neuronal NOS (160 kDa) and iNOS (130 kDa) were purified from the cytosol (Masters, 1994; Bredt and Snyder, 1994; Schmidt et al., 1991; Hevel et al., 1991; Stuehr et al., 1991), whereas the ecNOS (135 kDa) was found to be membrane-bound (Pollock et al., 1991). The nNOS and ecNOS are constitutively expressed, but modulated by intracellular $Ca^{2+}$ levels (Bredt and Snyder, 1990; Forstermann et al., 1991) unlike iNOS which is induced by bacterial endotoxin and is $Ca^{2+}$-independent (Cho et al., 1992). All three isoforms contain calmodulin and tetrahydrobiopterin ($BH_4$), as well as molar ratios of heme, FMN, and FAD (Hevel et al., 1991; Stuehr et al., 1991; Pollock et al., 1991; Mayer et al., 1991; White and Marletta, 1992; Stuehr and Ikeda-Saito, 1992; McMillan et al., 1992; Klatt et al., 1992). These members of the NOS family are unusual mammalian enzymes in that they catalyze both NADPH-mediated reduction of flavins and heme within the same protein. A cytochrome P450 fatty acid hydroxylase in *Bacillus megaterium* containing both flavins, FAD and FMN, in the same polypeptide chain as the heme has been reported by Narhi and Fulco (1986). Nitric oxide synthases, however, represent the first examples of such complex enzymes from mammalian sources.

Nelson et al. (1993) reportedly describes a relationship between the P450 gene superfamily and the nitric oxide synthase genes as a likely example of convergent evolution. While the nitric oxide synthases contain a carboxyterminal domain with sequence similarity to NADPH-P450 oxidoreductase (Bredt et al., 1991), and also possess heme and other biochemical features indicative of a P450-like function (White & Marletta, 1992), the nitric oxide synthases lack the P450 ten amino acid signature sequence present in 202 of 205 sequences compared in Nelson et al., 1993 and do not exhibit the characteristic I-helix present in all known cytochromes P450 (McMillen et al., 1992). Based on sequence alignments, the percent identity between mouse nitric oxide synthase and 57 cytochrome P450s was an average of 11.6%, about what would be expected for random amino acid sequences (Nelson et al., 1993).

Mechanistic and structure/function studies of nNOS have been very difficult to conduct due to the minute amounts of protein that can be purified from cerebellar tissue. Bredt and Snyder (1990) reported a yield of 9 μg of pure protein from 18 rat brains. Bredt, et al. (1991) subsequently cloned and expressed nNOS in human kidney 293 cells, providing a 10-fold enrichment of nNOS in cultured cells over rat brain. The expense and time involved in mammalian cell culture, however, are prohibitive for generating large amounts of enzyme. Other laboratories have expressed nNOS using baculovirus overexpression systems. Charles, et al. (1993) report successful expression, but the majority of this recombinant nNOS is insoluble and inactive; the recombinant enzyme has a specific activity that is 100-fold lower than that of native nNOS isolated from rat cerebellar tissue. Richards and Marletta (1994) improved the yield of active enzyme from the baculovirus system by adding hemin to the media, but still isolated only about 1 mg pure protein from seven to ten 75 $cm^2$ monolayer cultures, only about half of which contains heme. More recently, however, Riveros-Moreno et al. (1995) have been more successful with the baculovirus expression system, producing 30 mg of highly active enzyme per 17–225 $cm^2$ flask with one liter of media.

Nitric oxide is a short-lived molecule with a large number of roles, most of which are involved in signalling in the nervous and cardiovascular systems. In these cases, NO. acts by activating a soluble guanylate cyclase in the target cell, which leads to an intracellular accumulation of cyclic 3',5' guanosine monophosphate. This messenger molecule then activates a cascade of intracellular enzymes to bring about the biological effect, which ranges from relaxing isolated blood vessels to neurotransmission to neurodegeneration associated with decreased blood flow in AIDS dementia and Parkinson's disease (Ogden and Moore, 1995). In addition, NO. may act as a powerful reactive free radical that may contribute to the cytostatic and neurodegenerative effects of NO..

It is therefore advantageous, in certain circumstances, to inhibit the action of NOS as a means of reducing NO. production. Potential advantages of such inhibition include reducing the blood pressure loss that is associated with endotoxic shock, which has been shown to be associated with a large release of NO. arising from the cytokine-inducible NOS of macrophages. These large amounts of NO. have been shown to cause hypotension from uncontrolled vasorelaxation of vascular smooth muscle cells. Other investigators have shown that the selective inhibition of iNOS may be beneficial in treating some forms of inflammatory diseases.

Because numerous potential clinical applications for selective inhibition of both nNOS and iNOS isoforms have been identified, it is therefore advantageous to screen for inhibitors of NOS that will allow the development of new classes of compounds to block the deleterious effects of NO. in selected cells. While several techniques are known for screening for NOS inhibitors, a reliable and relatively inexpensive source of single isoform NOS has heretofore been unavailable.

Problems with the prior art methods of producing NOS include: i) insufficient amounts of protein produced, ii) expense and time involved in mammalian cell culture, iii) insolubility of expressed protein ("inclusion bodies"), iv) inactivity, v) low specific activity, and vi) insufficient incorporation of the many cofactors that are required for enzymatic activity. Because of all of the above problems, known procedures are not completely satisfactory, and persons skilled in the art have continued to search for improvements.

SUMMARY OF THE INVENTION

The present invention seeks to overcome these and other drawbacks inherent in the prior art by providing, for the first time, methods of producing large amounts of NOS or other proteins that are generally difficult to generate in sufficiently pure quantities. Moreover, the proteins produced using these methods are biologically reactivatable by the addition of one or more missing cofactors to yield the holoenzyme.

The methods of the present invention allow the production of large quantities of NOS in cultures of prokaryotic cells. Important elements of the host system include the vector (pCW), co-expression of folding agonists (or chaperonins) with nNOS, and a protease-deficient prokaryote as a host. The vector itself does not appear to be responsible for the heme incorporation capability of this system, since other heme-dependent enzymes, can be expressed using other vectors. This vector is, however, compatible with stable transfection of eukaryotic genes into various strains of E. coli. It is surprising and unexpected that a prokaryotic host, such as E. coli, has the ability to overexpress a complex mammalian enzyme such as nNOS, which contains protoporphyrin IX heme, FAD, FMN, and $BH_4$ as prosthetic groups. A further advantage of the present system is that calmodulin is not produced, thus precluding activation of the nNOS to produce the cytotoxin NO.. The lack of $BH_4$ in this system also serves to keep the enzyme "turned off" and so avoid the deleterious effects of NO. over production. Heme, FAD and FMN appear to be incorporated most favorably during protein biosynthesis; a process that is likely facilitated by chaperonins (folding agonists). The coexpression of calmodulin may be necessary for the expression of inducible NOS.

An important aspect of the present invention lies in the co-expression of chaperonins with NOS to result in a correctly folded protein that may be biologically reactivatable by the addition of one or more missing cofactors. The chaperonins are a distinct class of ubiquitous proteins that are highly conserved from bacteria to humans (Martinus et al., 1995). They appear to bind nonnative conformations of most proteins, thus preventing aggregation and subsequent inactivation. Chaperonins protect newly synthesized proteins during transport and folding, and, while expressed constitutively, synthesis may be enhanced by stress conditions, such as heat shock. As such, it has been shown that certain heat shock proteins, such as HSP6, HSP10, or HSP90 may serve as chaperonins. Representative examples of bacterial chaperonins include GroEL (E. coli chaperonin 60) and GroES (E. coli chaperonin 10, Hsp10). GroES has been found to be an essential component of the mitochondrial protein folding apparatus, and participates in various aspects of GroEL function (Hohfeld et al., 1994). Also contemplated as within the scope of the present invention is the use of eukaryotic chaperonins, such as CCT, also known as TCP-1 complex (Kim et al., 1994). This chaperonin is found in the eukaryotic cytosol and has unique structural features that correspond to the ATP-binding site of GroEL, while other regions show no significant identity in the region corresponding to the polypeptide-binding region of GroEL.

Thus, advantages of the present host construct for over-production of nNOS include: i) fast and inexpensive isolation of large quantities of enzyme, ii) the enzyme is as active as that from a mammalian source, iii) the activity can be controlled by the presence or absence of $BH_4$, iv) insolubility, aggregation, and proteolysis problems are substantially alleviated, and v) the expression system does not require highly specialized equipment other than the usual fermentation and sterilization facilities, vi) essentially pterin-free enzyme, useful for the investigation of the role of $BH_4$ in NOS function, may be easily produced.

The large amounts of intact, active nNOS that can be generated using this system will make possible the mechanistic, kinetic, and spectroscopic studies required for the understanding of structure/function relationships. This nNOS has a specific activity at least as high as that of kidney 293 cell-expressed enzyme. It is further contemplated that the approach outline set forth herein may also be useful for the overexpression of the other NOS isoforms, such as ecNOS and iNOS, in a prokaryotic system. The availability of this expression system for the NOS enzyme will be extremely useful for site-directed mutagenesis and, given the important physiological roles played by the NOS isoforms, drug design and development.

Also disclosed herein are methods of producing nitric oxide synthase, comprising first obtaining a protease-deficient prokaryotic cell that comprises a first nucleotide sequence that encodes a nitric oxide synthase, and a second nucleotide sequence that encodes a folding agonist. Each of the nucleotide sequences is under the control of a promoter, which may be an inducible or constitutive promoter, and the cells may be grown in the presence of heme precursor (δ-aminolevulinate) and flavin precursors. Nitric oxide synthase apoenzyme is isolated from the cell, and incubated with tetrahydrobiopterin for activation from apoenzyme to holoenzyme.

As used in the instant invention, the nucleic acid sequences encoding NOS may be from a variety of prokaryotic and eukaryotic sources. For example, Nakane et al. (1993) cloned and expressed human brain NOS and showed that it was active in skeletal muscle. In addition, Janssens et al. (1992) cloned and expressed human ecNOS, showing that it has close homology with the constitutively expressed brain nNOS, suggesting that ecNOS is a member of the constitutively expressed class of nitric oxide synthases. Lastly, Geller et al. isolated the gene for human hepatocyte iNOS and demonstrated that its activity is present in a wide variety of tissues. Utilizing the methods set forth by the instant inventors, these forms of NOS, as well as functionally equivalent proteins or peptides may be expressed. These functionally equivalent proteins or peptides may be created vial the application of recombinant DNA technology, in which changes in the protein structure may be engineered, based on consideration of the properties of the amino acids being exchanged.

In the methods of the present invention, the nucleotide sequence encoding NOS may be carried in an expression vector that contains nucleotide sequences encoding folding agonists, or the genes encoding folding agonists may be on a separate expression vector that is co-transfected with the vector that contains the NOS sequences.

It also is recognized that other large heme, flavin or other prosthetic group-containing proteins could be expressed using a combination of the techniques disclosed herein. For example, heme and flavin biosynthetic precursors are included in the present invention for nNOS expression.

As used herein, the term "apoenzyme" means an enzyme or protein part of an enzyme-cofactor complex that has lost an essential cofactor and is therefore inactive. In addition, the terms "a" and "an" mean "one or more" when used in this application, including the claims.

Nucleic Acid Equivalents

As used herein, the term "nucleic acid segment or fragment" is intended to refer to DNA or RNA molecules that have been isolated free from total genomic or total cellular nucleic acids. Included within the term "nucleic acid segment or fragment" are segments which may be employed in the preparation of vectors, as well as the vectors themselves, including, for example, plasmids, cosmids, phage, viruses, and the like. It will be understood that the present invention also encompasses sequences which are complementary to the sequences listed herein, along with biological functional equivalents thereof, including naturally occurring variants and genetically engineered mutants.

The DNA segments and recombinant vectors of the present invention may variously include the DNA coding regions set forth herein, coding regions bearing selected alterations or modifications in the basic coding region, or may encode larger or smaller polypeptides which nevertheless include sequences encoding functional nNOS.

The nucleic acid segments of the present invention, regardless of the length of the coding sequence itself, may be combined with other DNA sequences, such as promoters, polyadenylation signals, additional restriction enzyme sites, multiple cloning sites, prokaryotic ribosome binding sites, other coding segments, and the like, such that their overall length may vary considerably. It is contemplated that a nucleic acid fragment of almost any length may be employed, with the total length preferably being limited by the ease of preparation and use in the intended recombinant DNA protocol.

Recombinant Vectors

Recombinant vectors form important further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with NOS gene(s), e.g., in human cells, as may be obtained by isolating the 5' non-coding sequences located upstream of the coding segment or exon, for example, using recombinant cloning and/or PCR technology, in connection with the compositions disclosed herein.

Representative of the vectors that are suitable in the present invention is that described in U.S. Pat. No. 5,240,831 to Barnes, incorporated herein by reference, and Barnes et al., 1991, which describe a vector designated pCW that is adaptable for use with genes encoding the various cytochromes P450. While this vector was chosen because of successful use in expression of a variety of cytochromes P450, including several of the CYP4A gene subfamily, it is proposed that virtually any appropriate bacterial expression plasmid or vector may be employed where desired, at least as a starting point, for expression of NOS. This may include, but are not limited to, pKK (223-3, 233-2, 177-3, 240-11), pTrc99A–C, pDR540, pBK, pET, pRSET (A–C), pBC, pSE (280, 380, 420), pTrc HIS(A–C), pET 11 (a–d), pET 5 (a–c), PET 3 (a–d), pET9 (a–d), pET 12(a–c), pGEX (1–5) and the like.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a NOS gene in its natural environment. Naturally, it will be important to employ a promoter that effectively directs the expression of the DNA segment in the cell type chosen for expression. The use of promoter and cell type combinations for protein expression is generally known to those of skill in the art of molecular biology, for example, see Sambrook et al. (1989). The promoters employed may be constitutive, or inducible, and may be used under the appropriate conditions to direct high level expression of the introduced DNA segment, such as is advantageous in the large-scale production of recombinant proteins or peptides. Appropriate promoter systems contemplated for use in high-level expression include, but are not limited to, taq, lac, lac UV5, trc, lambda $P_L$, T7 or T3.

As mentioned above, in connection with expression embodiments to prepare recombinant NOS proteins and peptides, it is contemplated that longer DNA segments will most often be used, with DNA segments encoding the entire NOS protein or functional peptide fragments thereof being most preferred. However, it will be appreciated that the use of shorter DNA segments to direct the expression of NOS peptides or epitopic core regions, such as may be used to generate anti-NOS antibodies, also falls within the scope of the invention. In addition, the recombinant vectors and isolated segments may therefore variously include the NOS coding regions themselves, coding regions bearing selected alterations or modifications in the basic coding region, or may encode larger polypeptides which nevertheless include sequences that will confer NOS activity when expressed.

Recombinant Host Cells

The present invention also concerns recombinant host cells that include one or more DNA segments that comprise an isolated NOS gene, as described herein. It is contemplated that virtually any cell may be employed as a recombinant host cell, but that certain advantages may be found in using a bacterial host cell, such as, for example, in the ease of cell growth and manipulation. Examples of preferred bacteria for use as recombinant host cells include, for example, E. coli. Other suitable prokaryotic host cells include, but are not limited to, members of the gram negative family Enterobacteriaceae. Representative members of this family include Serratia, Salmonella, Pseudomonas, Shigella, Enterobacter, Proteus, and Erwinia.

Another important aspect of the invention is use of protease-deficient host cells for the expression of the construct. Exemplary E. coli strains include BL21, Y1089 and Y1090hsdR, which are lon⁻. Other E. coli strains that naturally lack lon include, but are not limited to, rpoH (h+pR), tsp, in which a deletion eliminates a periplasmic protease that may degrade overexpressed proteins following lysis, CAG597 (rpoH165), CAH626 (lon⁻), CAH629 (lon⁻), ER1458 (lon⁻), pR745 (lon⁻) and UT5600 (ompT⁻).

The recombinant host cells of the invention may be employed either to propagate the vector and/or to express the various peptides and proteins described herein, allowing the encoded components to be obtained essentially free of other human or mammalian components. That is, one may prepare such peptides or proteins by recombinant expression using a host cell other than human or mammalian, and/or produce the peptides or proteins at high levels so that their isolation directly results in a significantly enriched preparation.

Depending on the host system employed, one may find particular advantages where DNA segments of the present invention are incorporated into appropriate vector sequences that may, e.g., improve the efficiency of transformation of host cells. Where bacterial host cells are employed, it is proposed that virtually any vector known in the art to be appropriate for the selected host cell may be employed. Thus, in the case of E. coli, one may find particular advantages through the use of plasmid vectors such as pCW, pBR322, or bacteriophages such as λGEM-11. Further examples will be known to those of skill in the art, as exemplified in Sambrook et al. (1989).

The recombinant host cells may be employed in connection with "overexpressing" NOS proteins or peptides, that is, increasing expression over the natural expression levels in human or other mammalian cells, other bacterial expression systems, or baculovirus-directed systems, and may lead to the production of large quantities of proteins. Overexpression may be assessed by a variety of methods, including radio-labelling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide, in comparison to the level in natural human or mammalian cells, is indicative of overexpression. Obviously, if this is coupled to spectral identification and/or enzyme activity, the procedure is more thoroughly documented as to its useful efficacy in producing "active" protein. The utilization of spectral methods is particularly useful with NOS expression systems since heme incorporation into the biosynthesized protein is key to the success of the expression system.

Various methods may be used to obtain or collect NOS proteins or peptides from cells, whether native or recombinant. For example, one method involves lysing cells in the presence of protease inhibitors, centrifuging to remove debris, and applying the supernatant to a 2', 5'-ADP-Sepharose 4B column. Following washing, the protein is eluted in salt buffer containing 2'-AMP and further concentrated utilizing Centriprep membranes. The fractions are then incubated with L-arginine and $BH_4$, if $BH_4$-replete enzyme is desired, and further fractionated on a S-200 gel filtration column or MonoQ (ion exchange).

It will also be understood that this invention is not limited to the exact nucleic acid and amino acid sequences described herein. As a consequence, DNA segments prepared in accordance with the present invention may also encode biologically functional equivalent proteins or peptides which have variant amino acid sequences. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged, i.e., site-directed mutagenesis.

ABBREVIATIONS $BH_4$=tetrahydrobiopterin
ecNOS=endothelial cell isoform of NOS
iNOS=inducible macrophage isoform of NOS
NMA=N-methyl-L-arginine
NNA=$N^\omega$-nitro-L-arginine
NOS=nitric oxide synthase
nNOS=neuronal isoform of NOS

BRIEF DESCRIPTION OF THE DRAWINGS

The following drawings form part of the present specification and are included to further demonstrate certain aspects of the present invention. The invention may better be understood by reference to one or more of these drawings in combination with the detailed description of specific embodiments presented herein.

DETAILED DESCRIPTION OF THE PREFERRED EMBODIMENTS

Figure 1A:
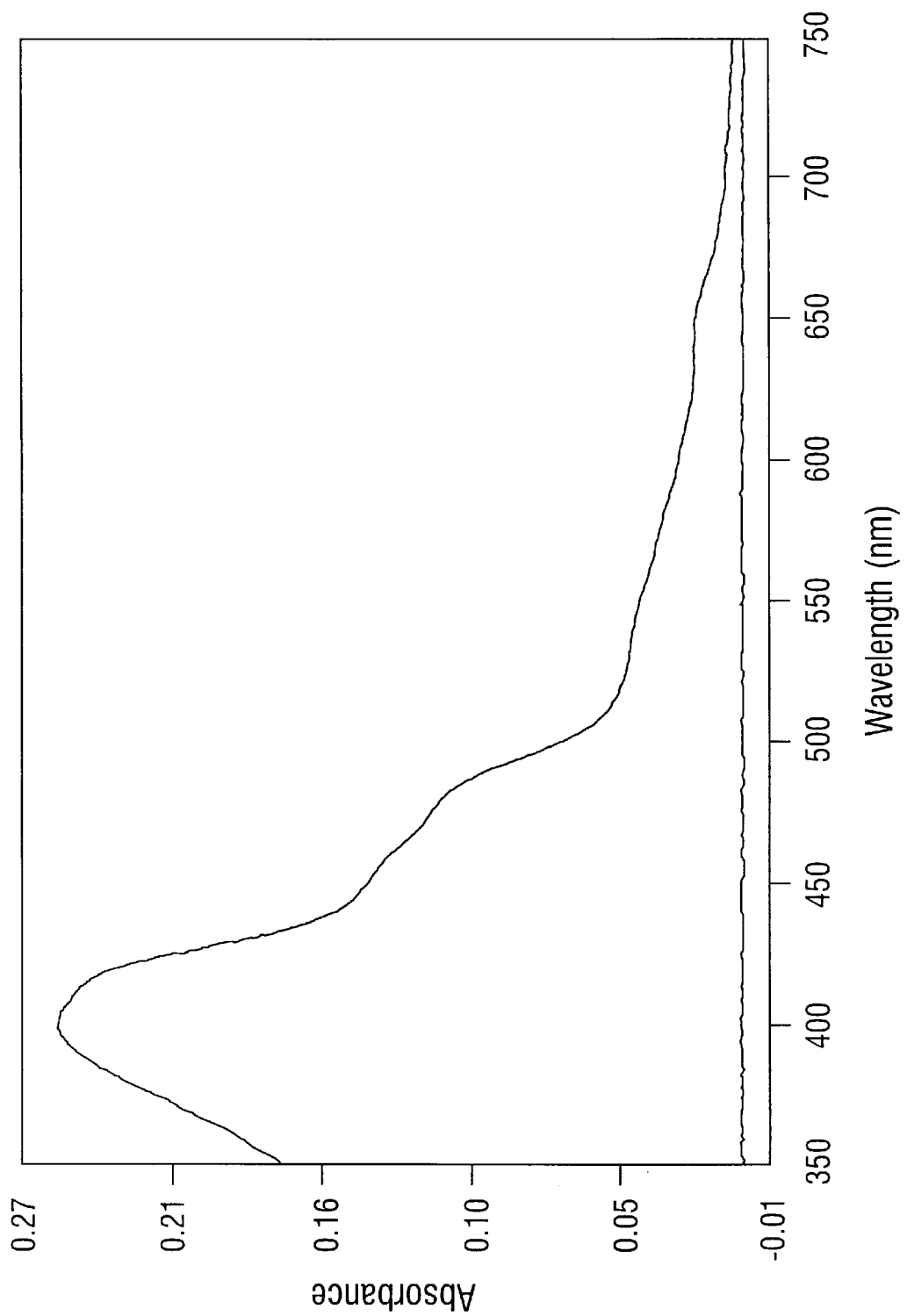
FIG. 1A shows absolute absorbance of nNOS as purified from E. coli. Studies were performed as described in Example 2 using 3.2 μM nNOS.

The present invention involves the successful overproduction of nitric oxide synthase (NOS) in a prokaryote. In particular, overexpression of functional neuronal NOS in Escherichia coli, with average yields of 125–150 nmol enzyme/liter of cells is provided in the present disclosure. An important aspect of the present invention is the subcloning of the cDNA for nNOS into a pCW vector under the control of the tac promotor and the co-expression of this construct with the chaperonins groEL and groES in a protease (-) BL21 strain of E. coli. The enzyme produced is replete with heme and flavins and, after overnight incubation with tetrahydrobiopterin, contains 0.7 pmol tetrahydrobiopterin/pmol nNOS. It is isolated as a predominantly high spin heme protein and demonstrates spectral properties which are identical to those of nNOS isolated from human kidney 293 cells.

The product of the NADPH-mediated reaction, NO., has been implicated in neurotransmission in the brain and in neuromuscular junctions (nNOS), hemodynamic regulation (ecNOS), and cytotoxicity (iNOS). The effects of NO. produced by the nNOS and ecNOS are thought to be mediated through the stimulation of guanylate cyclase activity, whereas the NO. or the product of its interaction with $O_2$., peroxynitrite (ONOO.), produced by iNOS appears to act directly on foreign cells (reviewed by Masters, 1994; Bredt and Snyder, 1994).

The isolated protein binds $N^\omega$-nitro-L-arginine, dependent on the presence of bound tetrahydrobiopterin, and exhibits a $k_d$ of 45 nM. Surprisingly, the enzyme is completely functional, with a specific activity of 450 nmol/min/mg. The overexpression system of the present invention is useful for rapid, inexpensive preparation of large amounts of active nNOS for use in mechanistic and structure/function studies, for use in screening candidate substances for inhibition of various forms of NOS, as well as for drug design and development.

The nNOS enzyme produced by E. coli appears to be indistinguishable, in all respects examined, from that produced by nNOS stably-transfected human kidney 293 cells; the absolute spectrum and its perturbation by the substrate L-arginine (spectral binding constant ≈717 nM), the CO difference spectrum, the binding constant for [$^3$H]-NNA (≈45 nM), and the specific activity of E. coli-expressed nNOS is at least equal to or greater than the mammalian cell-expressed nNOS.

The enzyme produced by the methods of the instant invention is quite active, with a turnover of 450 nmol/min/mg NOS, as measured by both the hemoglobin capture assay and the conversion of [$^3$H]-L-arginine to [$^3$H]-L-citrulline, and this activity is 95% inhibited by 100 μM NMA, indicating that NMA is effectively competing at the substrate binding site. The $K_m$ value of E. coli-expressed nNOS for L-arginine is 2.8 μM, in good agreement with both that of nNOS isolated from transfected human kidney 293 cells (≈2 μM) and that reported by Bredt and Snyder (1990) for nNOS isolated from rat brain (≈2 μM).

While fraction 2 (FIG. 4) seems to be fully complemented with $BH_4$, additional $BH_4$ added to the assay serves to increase enzyme activity further but not markedly. This may be due to the instability of $BH_4$ that is bound to the enzyme. The difference between the enzymatic activities exhibited by the pre-and post-$BH_4$ fractions, however, is 2-fold whether or not $BH_4$ is included in the assay. It appears that the earlier the nNOS is saturated with $BH_4$, the higher the activity, i.e., the more stable the enzyme.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Overproduction of Neuronal NOS in E. coli

The present example describes constructs and methods for the overproduction of functional neuronal nitric oxide synthase in E. coli."A deposit of plasmid NOSpCW in E. coli strain BL21 was made with the American Type Culture Collection, 12301 Parklawn, Rockville, Md., 20852, on Aug. 10, 1995, and has ATCC Accession No. 69881."

Chemicals. L-[2,3-$^3$H] arginine was obtained from DuPont NEN (Boston, Mass.), and (6R)-5, 6, 7, 8 tetrahydro-L-biopterin ($BH_4$) was from Research Biochemicals International (Natick, Mass.). All other chemicals were obtained from Sigma Chemical Co. (St. Louis, Mo.) and were of the highest grade available.

Enzymes. Taq polymerase, ligase, and restriction enzymes were from Promega (Cambridge, Mass.) or New England Biolabs (Boston, Mass.). Shrimp alkaline phosphatase was from United States Biochemical (Cleveland, Ohio).

Plasmids. pNOS (Bredt et al., 1991), containing the rat nNOS cDNA in Bluescript SK(−), was generously provided by Drs. Solomon Snyder and David Bredt at Johns Hopkins Medical School, Baltimore, Md. pGroESL (Goloubinoff et al., 1989), containing groEL and groES cDNAs, was a gift from Dr. Paul Horowitz at the UT Health Science Center in San Antonio, Tex. $pCW_{ori+}$ (Gegner and Dahlquist, 1991) was obtained by Dr. Michael Waterman at Vanderbilt University in Nashville, Tenn., and shared with us by permission. The production of nNOS is controlled by the tac promoter of pCW in an effort to abate a major drawback of the baculoviral system, poor heme incorporation. Since initial studies were plagued by highly proteolyzed and dysfunctional protein, an expression plasmid for the chaperonins groEL and groES (Wynn et al., 1994) was also included.

Recombinant DNA manipulations. nNOSpCW, the plasmid for the expression of nNOS in E. coli, was constructed as follows. The initial 1210 nucleotides of pNOS (from the ATG start codon to the NarI restriction site) were amplified by PCR to incorporate the recognition sequence for NdeI. Primer 1 (upstream primer, with NdeI site) was 5'-TCATCATCATATAACTGAAGAGAACACGTT-3' (SEQ ID NO: 1) and primer 2 (return primer) was 5'-CATGCTTGGCGCCAT-3' (SEQ ID NO: 2). Primers were synthesized by the Center for Advanced DNA Technologies at the UT Health Science Center at San Antonio. Reaction mixtures included 50 pmol of each primer, 20 ng pNOS template, 200 μM dNTPs, 1.5 mM $MgCl_2$, 1×Taq polymerase buffer, and 2.5 units Taq polymerase in 100 μl total volume. The mixture was preincubated for 3 minutes at 94° C. prior to the addition of Taq polymerase, followed by amplification for 30 cycles: 94° C. for 30 s, 55° C. for 60 s, and 72° C. for 90 s. The PCR product was gel-purified using the Gene/Clean II kit (Bio101, Vista, Calif.) and digested with NdeI and NarI. pNOS DNA was then restricted with NarI and XbaI to generate the remaining 3529 nucleotides of the NOS cDNA sequence, which was also gel-purified. $pCW_{ori+}$ DNA was digested with NdeI and XbaI and the ends were dephosphorylated. The three pieces were ligated, and the resultant products were used to transform E. coli JM109 competent cells (Stratagene, San Diego, Calif.) using the manufacturer's instructions.

The transformation mixture was plated on LB agar containing 50 μg/ml ampicillin and nine colonies were screened by BamHI restriction digest of alkaline lysis plasmid minipreparations. Five positive clones were further screened for IPTG-induced (0.5 mM, added at $OD_{600}$=0.8, along with 225 μM δ-aminolevulinic acid, a heme precursor) expression of nNOS at 37° C. by immunoblot analysis of whole cells using rabbit anti-rat nNOS IgG. All five clones exhibited bands which co-migrated with that of nNOS isolated from kidney 293 cells.

In subsequent manipulations, when pGroELS was co-transformed with nNOSpCW, transformants were plated on LB agar containing 50 μg/ml ampicillin and 35 μg/ml chloramphenicol. Due to severe proteolysis of nNOS when JM109 cells were lysed, both plasmids were also co-transformed into the protease-deficient E. coli strain BL21. Transformation of BL21 was via electroporation using an Invitrogen Electroporator II (San Diego, Calif.) according to manufacturer's instructions.

Protein expression. Fernbach flasks containing 1 liter of modified Terrific Broth (20 g yeast extract, 10 g bactotryptone, 2.65 g $KH_2PO_4$, 4.33 g $Na_2HPO_4$, 4 ml glycerol) and 50 μg/ml ampicillin and, when pGroELS was present, 35 μg/ml chloramphenicol were inoculated with 1 ml of an overnight culture (grown in LB+antibiotics) and shaken at 250 rpm at 37° C. Protein expression was induced at $OD_{600}$=1.0–1.4 with the addition of IPTG to 0.5 mM. The heme and flavin precursors, δ-aminolevulinic acid and riboflavin, were also added to final concentrations of 450 μM and 3 μM, respectively. When pGroELS was present, ATP to 1 mM was also added to the culture media. The flasks were moved to room temperature (25° C.) and shaken in the dark at 250 rpm. The cells were harvested at about 40 hours post-induction in the cell paste frozen at −80° C. until purification.

JM109 cells containing pNOSpCW grown post-induction at 37° C. exhibit no detectable peak at 445 nm in CO difference spectra; all protein is present as a 420 nm species. JM109 containing pNOSpCW grown at 25° C. for 36–40 hours post-induction have both 445 and 420 nm species; this protein is heavily proteolyzed upon cell lysis, as judged by immunoblot analysis. The absolute amount of protein production in JM109 is enhanced 5–10-fold upon co-expression of nNOS with groEL and groES, but this protein is still heavily proteolyzed upon cell lysis. A small amount of activity (1% that of nNOS purified from 293 cells) can be detected. BL21 cells containing pNOSpCW do not appear to express nNOS as detectable by CO difference spectra. BL21 cells containing both pNOSpCW and pGroELS, however, produce 125–250 moles nNOS (20–24 mg) per liter of culture, as quantitated by CO difference spectra. All data presented in Examples 1–5 are derived using protein purified from BL21 that has been co-transformed with both pNOSpCW and pGroELS.

Protein purification. Harvested cells were resuspended in 30 ml of resuspension buffer (100 mM Tris-HCl, pH 7.4, 1 mM EDTA, 1 mM dithiothreitol, 10% glycerol, 1 mM phenylmethylsulfonyl-fluoride, and 5 μg/ml leupeptin/pepstatin) per liter of initial culture and were lysed by pulsed sonication (four minutes, 80% power, large probe, Fisher Scientific Model 550). Cell debris was removed by centrifugation at 150,000×g for 70 minutes. The supernatant was applied to 2'5'-ADP-Sepharose 4B column (6 ml, Pharmacia) equilibrated in buffer B (50 mM Tris-HCl, pH 7.4, 0.1 mM EDTA, 0.1 mM dithiothreitol, 10% glycerol, and 100 mM NaCl). The column was extensively washed with at least 10 column volumes of buffer B, and then again with buffer B containing 500 mM NaCl. The protein was eluted with buffer B containing 500 mM NaCl and 5 mM 2'-AMP. The colored fractions were pooled and concentrated (Centriprep 30, Amicon), and L-arginine and $BH_4$ were added to final concentrations of 2 mM and 1 mM, respectively. This fraction was incubated overnight at 4° C. and applied to a S-200 gel filtration column (480 ml, 2.5 cm diameter, Pharmacia) equilibrated in buffer B. The nNOS-containing fractions were pooled, concentrated, and stored at −80° C. All manipulations were performed at 4° C. At this point, the enzyme is approximately 70% pure, with only one other major contaminant. Substitution of MonoQ ion exchange for the S200 gel filtration chromatography step results in an about 90% pure product.

In the present invention, nNOS is co-expressed with the E. coli groE molecular chaperonin system (groEL and groES). In the absence of these proteins, expression of nNOS is much lower in E. coli strain JM109 and undetectable in E. coli BL21. Chaperonins facilitate the proper folding of some proteins, probably by inhibiting aggregation and/or by alleviating kinetic blocks to folding. The expression of correctly folded proteins is not necessarily assisted by the presence of chaperonins. For example, Lah et al. (1994) have shown that cosynthesis of GroEl and GroES chaperonin with phagemid-produced antibody fragments fused to a bacteriophage coat protein resulted in complete proteolysis of the fusion product. The observation that substantially more nNOS is produced in the presence of chaperonins utilizing the methods and compositions of the instant invention further demonstrates the utility of this approach.

The E. coli strain JM109 was initially chosen for the expression of nNOS but, upon lysis of the cells, the calmodulin binding site proved to be extremely susceptible to proteolytic attack. As a result of this sensitivity, large amounts of the proteolytically-produced domains of E. coli-expressed nNOS were initially purified, a problem which was alleviated by co-expressing the nNOS and chaperonins in BL21, a strain reported to be lacking both lon and ompT proteases and which apparently also makes significantly more tetrahydrobiopterin that the commonly used JM109. When the calmodulin-binding site is covered by calmodulin, no digestion by trypsin is observed (Sheta et al., 1994) at this site but other susceptible sites are cleared.

EXAMPLE 2

Spectral Properties of Overproduced nNOS

The present Example demonstrates spectral characteristics of the overproduced neuronal NOS.

Spectrophotometric methods. Absolute spectra and CO difference spectra were performed essentially as described by McMillan and Masters (1993) with the exception that all measurements were performed in buffer B and the CO difference spectra were obtained by reducing the protein and then bubbling the sample cuvette with CO. Substrate perturbation difference spectra were performed as described (McMillan and Masters, 1993), but in the presence of 1 mM imidazole to shift the entire population of nNOS to the low spin heme state. The molar protein concentration was determined based on heme content and $\Delta\epsilon_{444-475}$=75 $mM^{-1}$ (Stuehr and Ikeda-Saito, 1992; McMillan and Masters, 1995). All spectral analyses were performed using a Shimadzu Model 2101 UV/visible dual-beam spectrophotometer.

Determination of heme content. The heme content of the purified protein preparation was measured by CO difference spectra and by the pyridine hemochromogen method (Rieske, 1967). A 30-μl aliquot of pyridine was added to 70 μl of purified protein, along with 1.5 μl 10N NaOH. The sample was reduced with two grains of dithionite and the spectrum read after two minutes. Heme concentration was determined by the absorbance at 556 nm, assuming ε=34 $mM^{-1}$.

Figure 2:
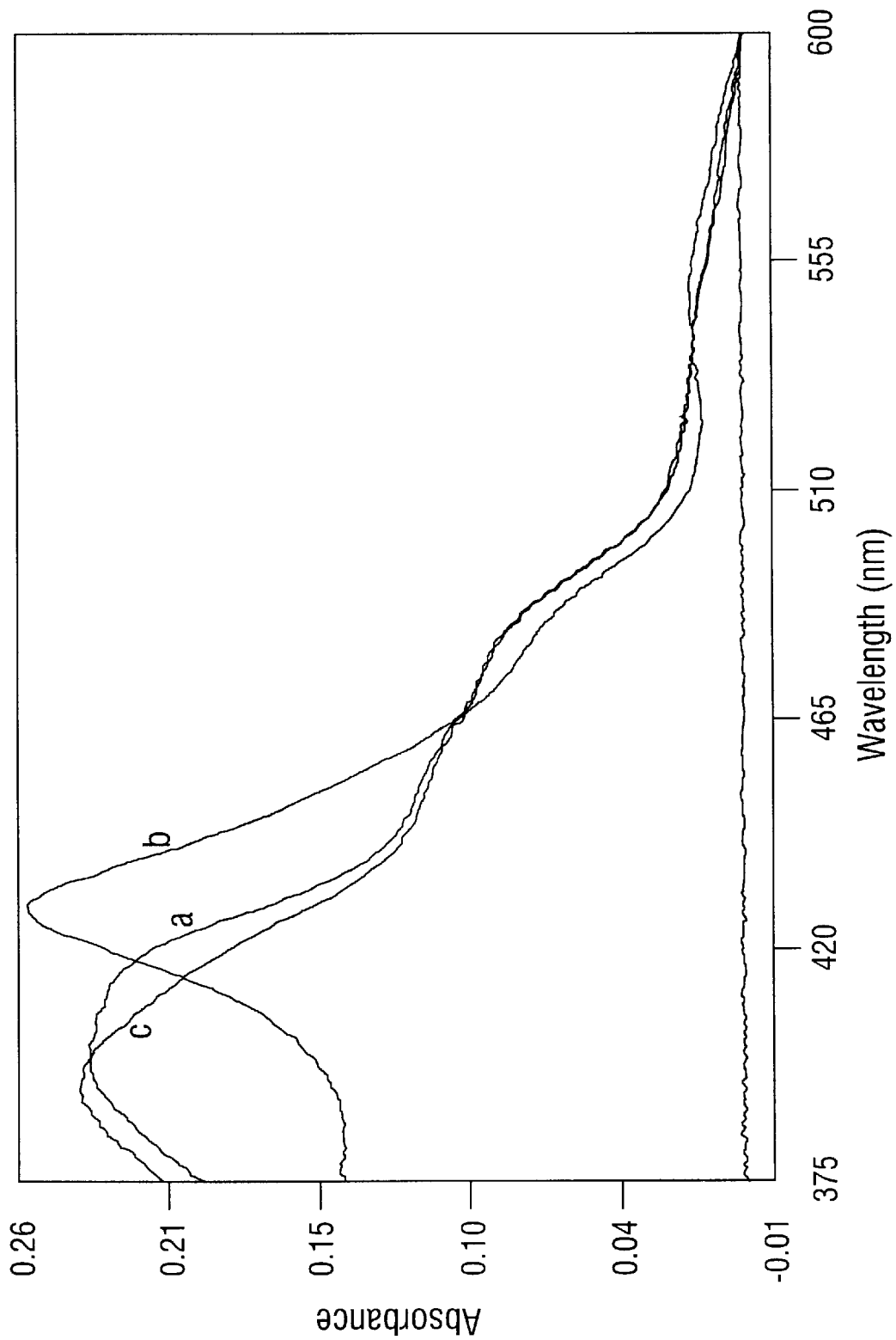
FIG. 2 shows perturbation of E. coli-expressed nNOS absolute absorbance spectrum. Studies were performed as described in Example 2 using 3.2 μM nNOS. Line a is the unperturbed spectrum of purified nNOS; line b is the spectrum following the addition of 1 mM imidazole to nNOS; and line c is the spectrum following the addition of 2 μM L-arginine to nNOS.
Figure 3A:
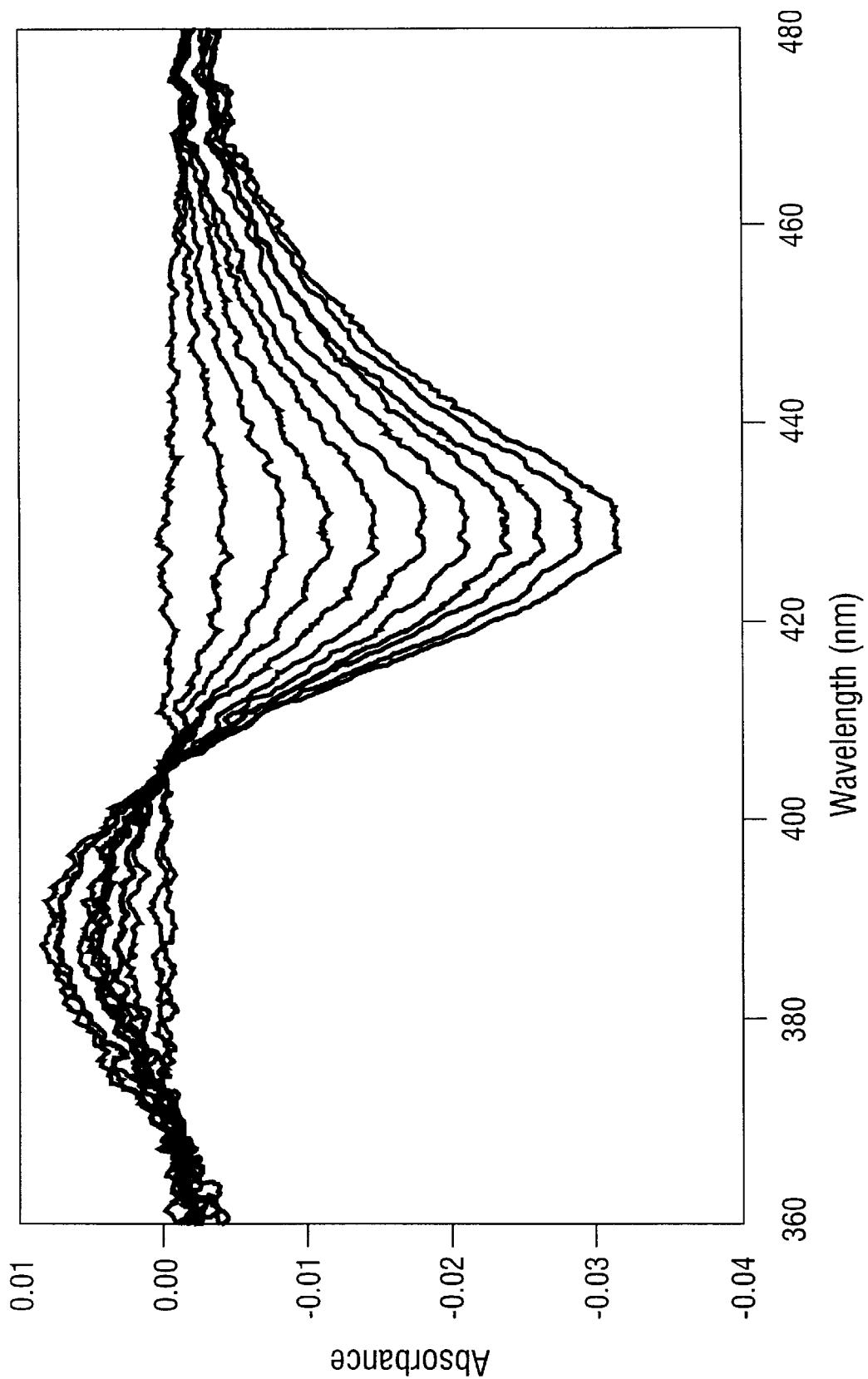
FIG. 3A shows substrate perturbation difference spectra of E. coli-expressed nNOS. Studies were performed as described in Example 2 using 1.5 μM nNOS in the presence of 1 mM imidazole. The purified enzyme was titrated with L-arginine to final concentrations of 0, 0.2, 0.4, 0.6, 0.8, 1.0, 1.2, 1.4, 1.6, 1.8, and 2.0 μM (baseline and sequential minima, respectively).
Figure 3B:
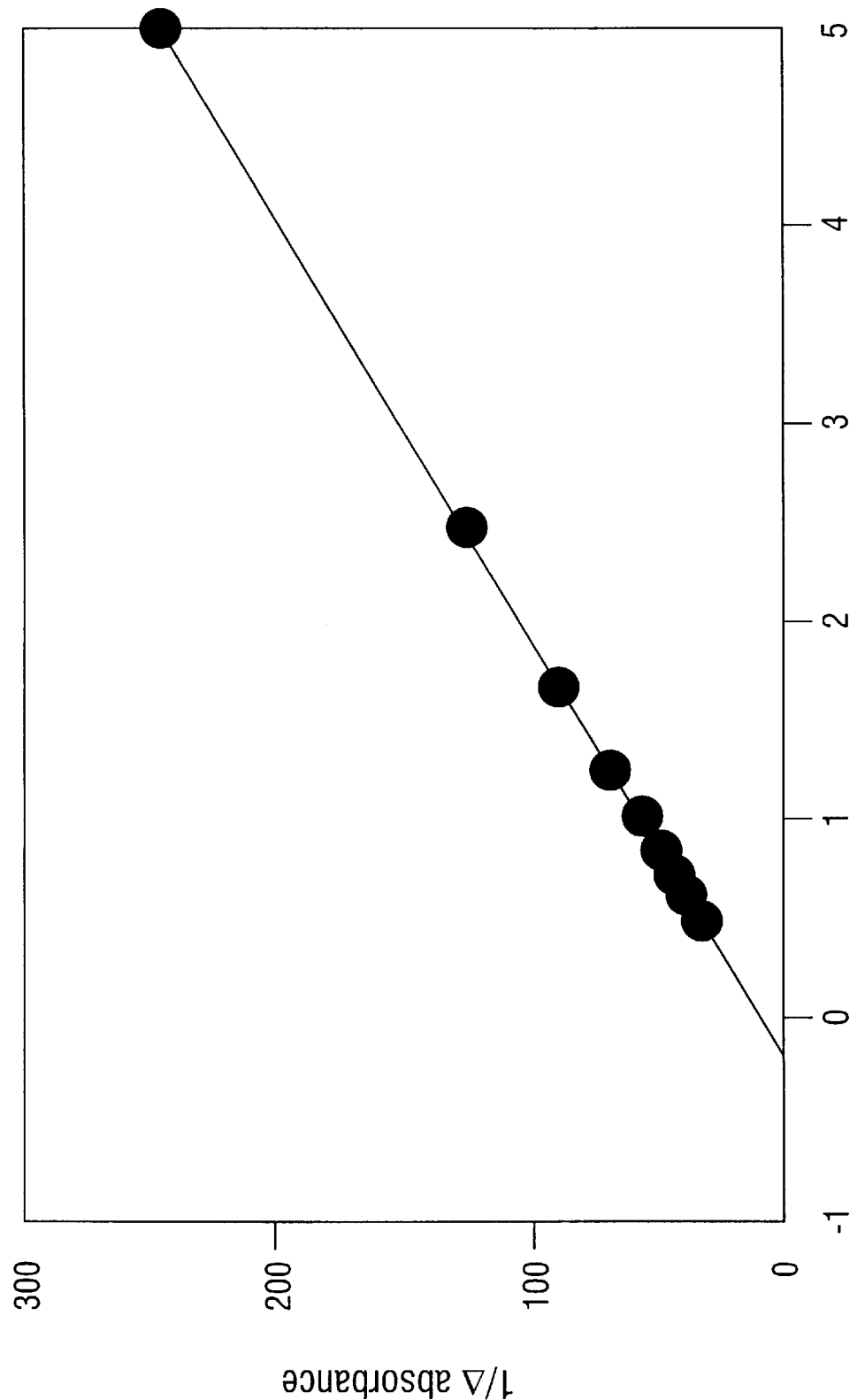
FIG. 3B shows a plot from which the apparent $K_S$ was derived using the data of FIG. 3A.

Spectral characteristics of purified E. coli-expressed enzyme. FIG. 1A shows the absolute spectrum of nNOS isolated from E. coli. It exhibits a broad peak at 400 nm and secondary maxima at 550 and 650 nm, indicative of a predominantly high spin heme, although some low spin form is present, as evidenced by the shoulder at 410 nm. Shoulders are also apparent at 450 and 475 nm and are due to flavin absorbance; this spectrum is identical to that of nNOS isolated from human kidney 293 cells (McMillan et al., 1992). As shown in FIG. 2, the maximum heme absorbance at 400 nm can be shifted to the low spin form (peak at 428 nm) by the addition of imidazole to 1 mM or completely to the high spin form (peak at 395 nm) by the addition of arginine to 2 μM.

Figure 1B:
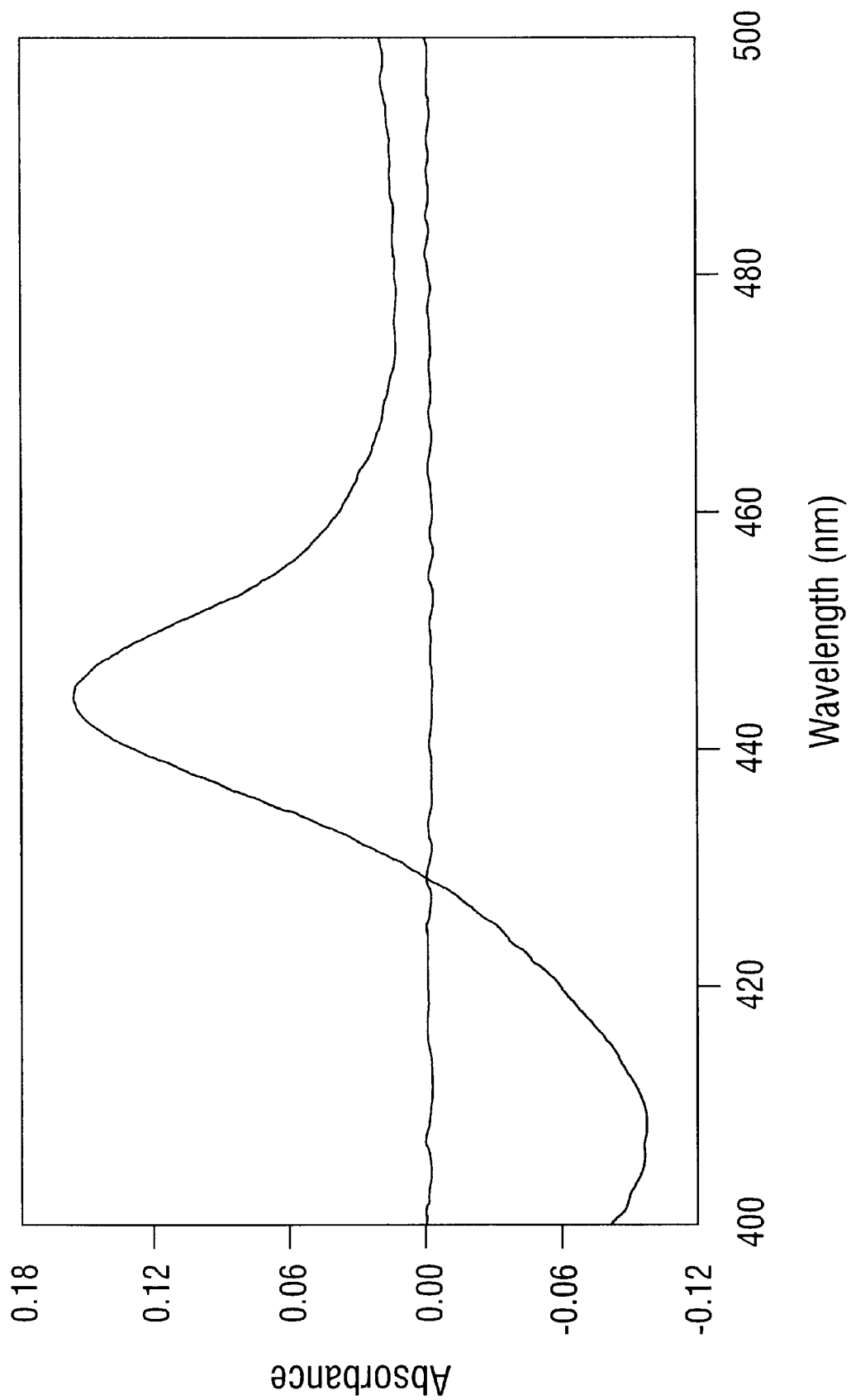
FIG. 1B shows CO difference spectra of nNOS as purified from E. coli. Studies were performed as described in Example 2 using 1.9 μM nNOS.

FIG. 1B shows the CO difference spectrum of nNOS with a peak at 444 nm. The molar concentration of heme-containing enzyme, calculated from the peak at 444 nm assuming $\Delta\epsilon_{444-475}=75$ mM$^{-1}$ is 1.9 $\mu$M. For comparison, a pyridine hemochromogen spectrum was also obtained to determine the heme concentration yielding a concentration of 2.1 $\mu$M, in reasonable agreement with that calculated from the reduced, co-difference spectrum.

Using the technique of difference spectrophotometry, the perturbation of the heme spectrum by increments of L-arginine, in the presence of 1 mM imidazole, was measured (FIG. 2A). A "type I" spectrum, characterized by a maximum at about 390 nm and a minimum at about 430 nm, was observed with each addition of L-arginine. A spectral binding constant ($K_S$) was calculated from the apparent $K_S$, derived from a plot of 1/absorbance change vs. 1/[L-arginine] (FIG. 2B), using the following:

apparent $K_S = K_S$ (1+[Imidazole]/$K_{d\ imidazole}$).

Assuming $K_{d\ imidazole}$ to be 160 $\mu$M (McMillan and Masters, 1993; Wolff et al., 1993), the value of $K_S$ for arginine binding to nNOS is 717 nM.

The heme moiety appears to be inserted correctly into the majority of expressed nNOS protein, as judged by the absolute and CO difference spectra and the spectral perturbation by the substrate L-arginine. The lack of heme-repletion, which seems to be a major drawback of the expression of NOS in a baculovirus system (Charles et al., 1993; Richards and Marletta, 1994), is overcome by expression in E. coli. There is ample evidence that the expression of cytochromes P450 in baculovirus systems results in heme-depleted product that, in some cases, can be remedied by the addition of hemin or precursors of heme in the porphyrinogenic pathway.

EXAMPLE 3

Pterin Content of Overproduced nNOS

Apoenzyme (nNOS without the cofactor $BH_4$) can be purified from the expression system of the present invention, and, upon incubation with BH4, is reconstituted to form the holoenzyme.

Pterin analysis. Determination of pterin content was performed as described by Gross and Levi (Gross and Levi, 1992), based on the method of Fukushima and Nixon (Fukushima and Nixon, 1980), by acid hydrolysis of 10 ng protein sample followed by quantitation of pterin by C18 reverse phase HPLC.

Pterin analysis of purified E. coli-expressed enzyme. Pterin content was determined in two different samples of nNOS: 1) partially purified enzyme before $BH_4$ incubation (fraction 1; pre-S-200 column chromatography); 2) purified enzyme after $BH_4$ incubation (fraction 2; post-S-200 column chromatography). The analysis reveals that, as isolated, fraction 1 contains 0.096 pmol $BH_4$/pmol nNOS, i.e., 10% of the expressed nNOS contains $BH_4$. No other pterin moiety was present. This is in contrast to the nNOS heme domain expressed in E. coli JM109, which contained only 1–2% $BH_4$, as well as being ≈30% saturated with non-$BH_4$ pterin. $BH_4$ is required for optimal activity of nNOS as shown in the present invention, but its role in the mechanism of NOS activity catalyzed by any of the isoforms is not presently known (Mayer et al., 1991); Schmidt et al., 1992); Marietta, 1993). Fraction 2 was complemented with 0.636 pmol $BH_4$/pmol nNOS, i.e., 64% saturated. Thus, if stoichiometric binding of $BH_4$ is required for activity, this preparation of nNOS contains 64% active enzyme.

EXAMPLE 4

Binding of Substrate Analog to Overproduced nNOS

The present Example demonstrates that binding of a substrate analog is dependent upon the presence in the enzyme of the cofactor, tetrahydrobiopterin.

Determination of $N^\omega$-nitro-L-arginine binding constant. The $N^\omega$-nitro-L-arginine (NNA) binding constant was determined by direct titration of purified nNOS with [$^3$H]-NNA. In these studies, performed in 96-well PVDF plates in 100 $\mu$l total volume, 10 pmol nNOS and radiolabeled NNA (specific activity ≈23,000 dpm/pmole) were incubated at room temperature for 15 minutes in 50 mM Tris-HCl, pH 7.6, 1 mM dithiothreitol, in the presence or absence of 10 $\mu$M $BH_4$. Assays were also performed in the presence or absence of 100 $\mu$M N-methyl-L-arginine (NMA), a potent inhibitor of L-arginine binding. The incubation was stopped by aspiration of the sample through the PVDF membrane. The wells were washed twice with 200 $\mu$l of 50 mM Tris, pH 7.6, air-dried for 10 minutes, 25 $\mu$l scintillation cocktail was added, and samples were counted.

Figure 4:
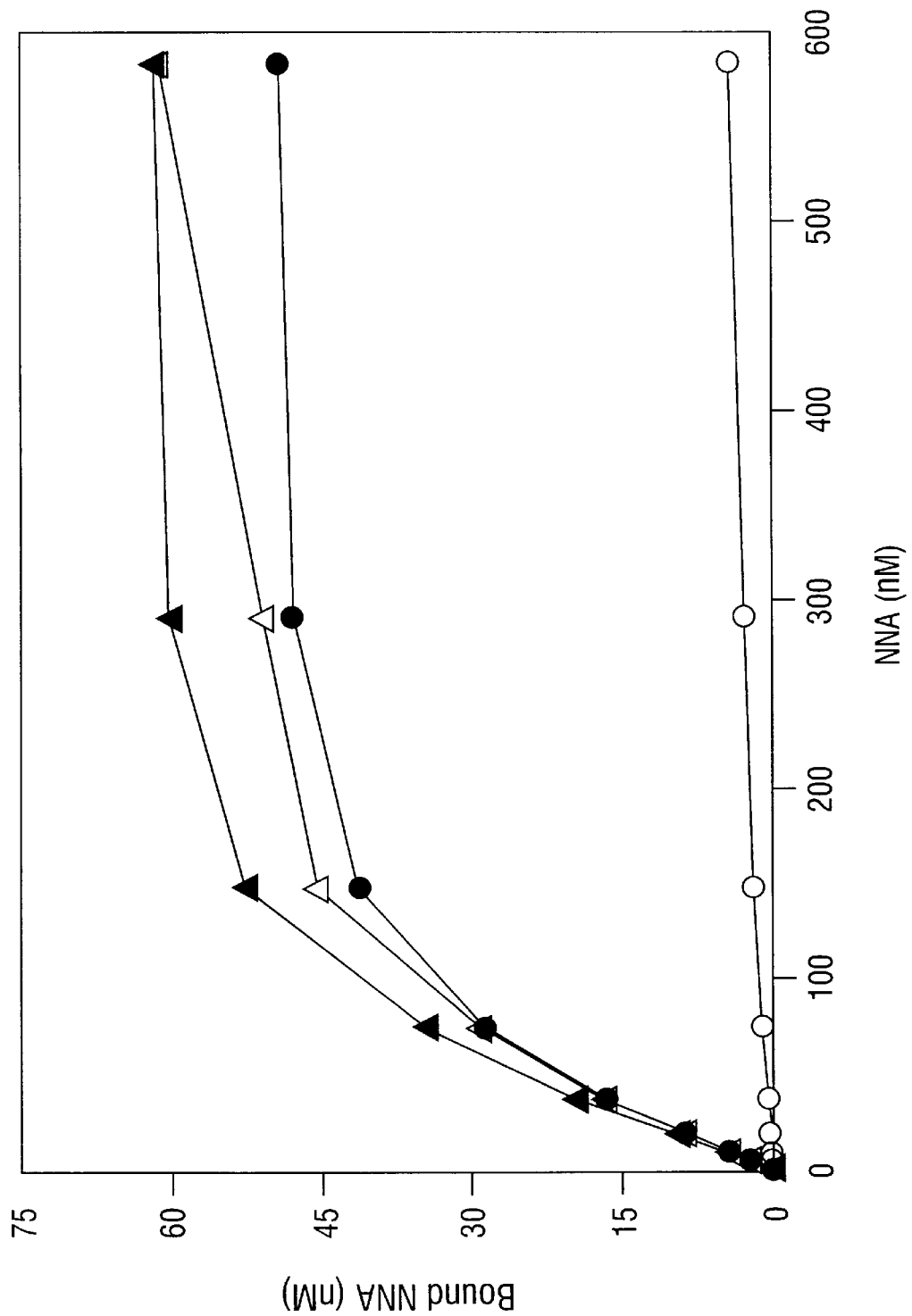
FIG. 4 shows binding of [$^3$H]-$N^\omega$-nitro-L-arginine to E. coli-expressed nNOS. Studies were performed as described in Example 4 using 10 pmole nNOS. Symbols are: circles, semi-purified E. coli-expressed nNOS eluted from a 2'5'-ADP-Sepharose 4B column in the absence of $BH_4$ during purification; triangles, purified E. coli-expressed nNOS purified in the presence of $BH_4$ as described in Example 1; open symbols represent data from assays performed in the absence of additional $BH_4$; filled symbols represent data from assays performed in the presence of 10 μM $BH_4$.
Figure 5:
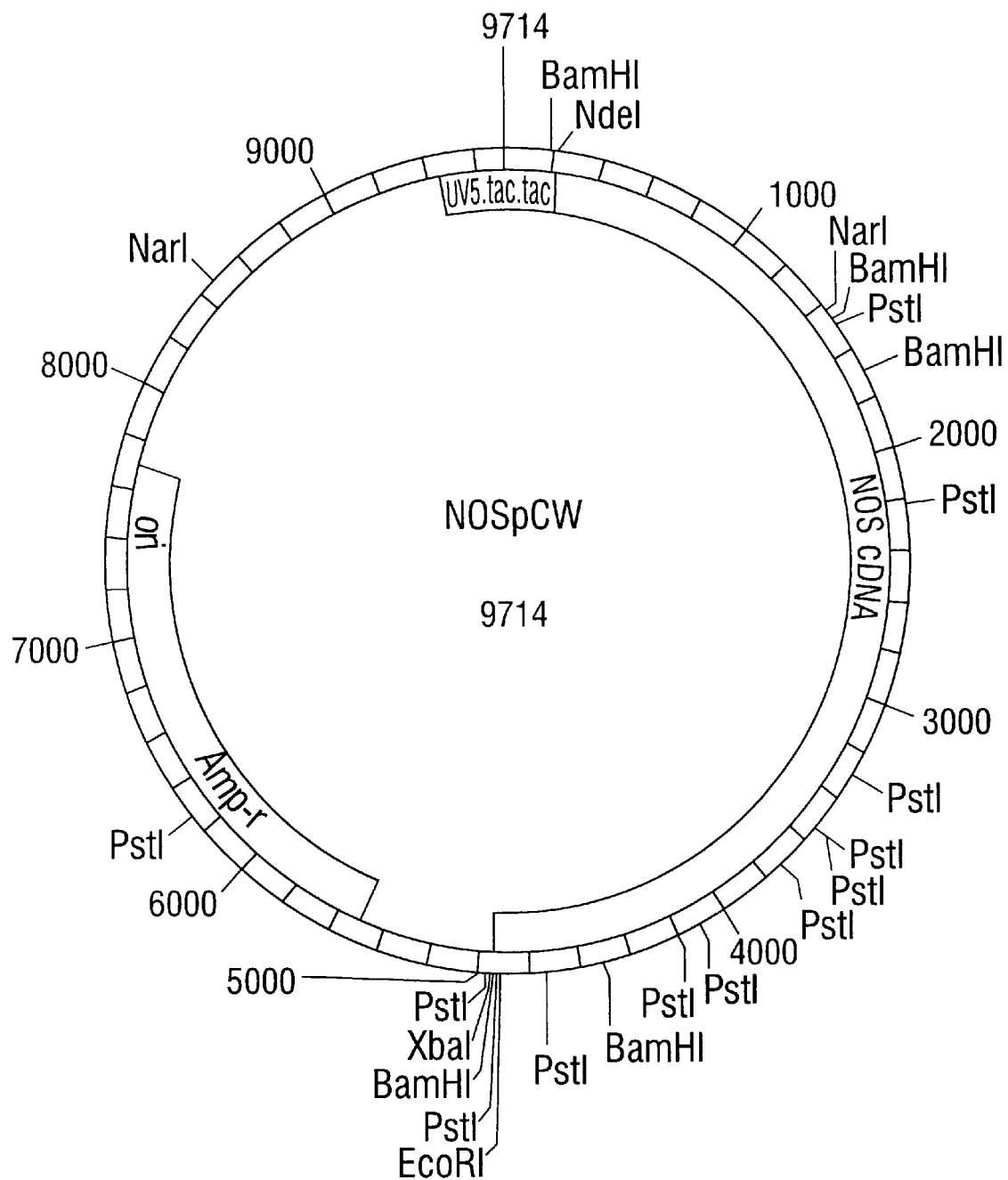
FIG. 5 shows an example of the plasmid construct NOSpCW used in the instant invention.

Binding of $N^\omega$-nitro-arginine to purified E. coli-expressed enzyme. The binding of [$^3$H]-NNA as a function of ligand concentration was determined in the presence and absence of additional $BH_4$ for both fractions 1 (pre-$BH_4$) and 2 (post-$BH_4$). As shown in FIG. 4 and Table 1, NNA binds significantly to E. coli-expressed nNOS fraction 1 only in the presence of added $BH_4$. The binding constant ($k_d$) and the maximum amount of NNA bound ($B_{max}$) differ greatly depending on whether or not $BH_4$ is added shown in Table 1. Fraction 2, which is 65% $BH_4$-saturated, binds NNA equally well in the presence or absence of added $BH_4$; $k_d$ and $B_{max}$ are the same regardless of whether $BH_4$ is added or not. In the presence of 100 $\mu$M N-methyl-L-arginine (L-NMA), the binding of NNA is essentially abolished in either fraction. Thus, NNA binding is dependent on the presence of bound $BH_4$ and the $k_d$ for NNA binding is approximately 45 nM. In addition, fraction 1 enzyme can be reconstituted with $BH_4$ up to 54% and fraction 2 enzyme does not bind additional $BH_4$, i.e., it appears to be maximally complemented.

TABLE 1

|  | $k_d$ (Nm) | $B_{max}$ (pmol NNA/pmol nNOS) |
|---|---|---|
| Fraction 1 |  |  |
| (+) $BH_4$ | 41 | 0.54 |
| (−) $BH_4$ | 483 | 0.078 |
| Fraction 2 |  |  |
| (+) $BH_4$ | 37 | 0.69 |
| (−) $BH_4$ | 58 | 0.67 |

EXAMPLE 5

Enzymatic Activity of Overproduced nNOS

The present example demonstrates that the rat neuronal NOS overexpressed in E. coli is functional in having a specific activity equal to or exceeding the activity of kidney 293 cell-derived enzyme.

Enzymatic activity determined by the rate of NO. formation. The rate of nitric oxide formation was measured using both the hemoglobin capture assay (Kelm and Schrader, 1990), performed at 25° C. as described by Sheta, et al. (1994), and the method of Bredt and Snyder (1990), which monitors the formation of [$^3$H] L-citrulline from [$^3$H] L-arginine, as described previously (McMillan et al., 1992). Each reaction mixture, containing 0.5 mg of enzyme, was incubated at 25° C. for 2 minutes (over which time the reaction is linear). For $K_m$ analysis, the concentration of [$^3$H] L-arginine in the reaction mixture was varied over the range of 2.0–10.0 μM.

Enzymatic activity of purified E. coli-expressed enzyme. The conversion of L-arginine to L-citrulline was assayed for fractions 1 (pre-BH$_4$) and 2 (post-BH$_4$) in the presence and absence of additional BH$_4$. The turnover numbers for fraction 1 were 75 and 202 nmole/min/mg without and with BH$_4$ in the assay mixture, respectively, a stimulation of 2.7-fold. The turnover numbers for fraction 2 were 189 and 435 nmole/min/mg without and with BH$_4$ in the assay mixture, respectively, a stimulation of 2.3-fold. The enzymatic activity is inhibited by 95% by NMA in all cases; this is consistent with the inhibition of NNA binding by NMA. The turnover numbers for both fractions in the presence of BH$_4$ were confirmed using the hemoglobin capture assay (previous paragraph); the activities of fractions 1 and 2 were 239 and 468 nmol/min/mg, respectively, demonstrating excellent agreement between the two methods. These turnover numbers are very similar to those obtained with nNOS purified from human kidney 293 cells in which activities between 300 and 450 nmole/min/mg are typically observed.

The $K_m$ value for L-arginine was determined to be 2.8 μM for E. coli-purified nNOS. Concomitant measurement using human kidney 293 cell-purified nNOS yielded a $K_m$ value of 1.9 μM. These values are in excellent agreement with each other and with the Km value of 2 μM for nNOS reported by Bredt and Snyder (1990).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Barnes et al., Proc. Natl. Acad. Sci. U.S.A., 88:5597–5601, 1991.
Bredt et al., Nature, 351:714–718, 1991.
Bredt and Snyder, Proc. Natl. Acad. Sci. USA, 87:682–685, 1990.
Bredt and Snyder, Annu. Rev. Biochem., 63:175–195, 1994.
Charles et al., Biochem. Biophys. Res. Commun., 196:1481–1489, 1993.
Cho et al., J. Exp. Med., 176:5991 604, 1992.
Forstermann et al., Proc. Natl. Acad. Sci. USA, 88:1788–1792, 1991.
Fukushima and Nixon, Anal. Biochem., 102:176–188, 1980.
Goloubinoff et al., Nature, 337:44–47, 1989.
Gegner and Dahlquist, Proc. Natl. Acad. Sci. U.S.A., 88:750–754, 1991.
Geller et al., Proc. Natl. Acad. Sci. USA, 90:3491–3495, 1993.
Gross and Levi, J. Biol. Chem., 267:25722–25729, 1992.
Hevel et al., J. Biol. Chem., 266:22789–22791, 1991.
Hohfeld, J., and Hartl, F. U. J. Cell Biol. 126:305–315, 1994.
Janssens et al., The Journal of Biological Chemistry, 267:14519–14522, 1992.
Kelm and Schrader, Circ. Res., 66:1561–1575, 1990.
Kim, S., Willison, K. R., Horwich, A. K. Trends Biochem. Sci. 19:543–548, 1994.
Klatt et al., Biochem. J., 288:15–17, 1992.
Lah, M., Addstraw, A., White, J. F., Dolezal, O., Malby, R., Hudson, P. J. Hum. Antibodies Hybridomas 5:48–56, 1994.
Lamas et al., Proc. Natl. Acad. Sc. USA, 89:6348–6352, 1992.
Lowenstein et al., Proc. Natl. Acad. Sci. USA, 89:6711–6715, 1992.
Masters, Ann. Rev. Nutr., 14:131–145, 1994.
Marletta, J. Biol. Chem., 2681:12231–12234, 1993.
Martinus, R. D., Ryan, M. T., Naylor, D. J., Herd, S. M., Hoogenraad, N. J., Hoj, P. B., FASEB J. 9:371–378. 1995.
Mayer et al., FEBS Lett., 288:187–191, 1991.
McMillan and Masters, Biochemistry, 32:9875–9880, 1991.
McMillan and Masters, Biochemistry, 34:3686–3693, 1995.
McMillan et al., Proc. Natl. Acad. Sci. USA, 89:11141–11145, 1992.
Nahri and Fulco, J. Biol. Chem., 269:15147–15153, 1986.
Nakane et al., Federation of European Biochemical Societies, 316:(no. 2) 175–180, 1993.
Nelson et al., 1995.
Nelson et al., DNA Cell Biol., 12:1–51, 1993.
Ogden, J. E. and Moore, P. K., Tibtech 13, 1995.
Pollock et al., Proc. Natl. Acad. Sci. USA, 88:10480–10484, 1991.
Richards and Marletta, Biochemistry, 33:14723–14732, 1994.
Rieske, Methods Enzymol., 10:488–493, 1967.
Riveros-Moreno, V., Hefferman, B., Torres, B., Chubb, A., Charles, I. and Moncado, S., Eur. J. Biochem., 230:52–57, 1995.
Sambrook, et al., Molecular Cloning, A laboratory Manual, 2nd Ed., 1989. Cold Spring Harbor Laboratory Press, N.Y.
Schmidt et al., Biochemistry, 31:3243–3249, 1992.
Schmidt et al., Proc. Natl. Acad. Sci. USA, 88:365–369, 1991.
Sessa et al., J. Biol. Chem., 267:15274–15276, 1992.
Sheta et al., J. Biol. Chem., 269:15147–15153, 1994.
Stuehr et al., Proc. Natl. Acad. Sci. USA, 88:7773–7777, 1991.
Stuehr and Ikeda-Saito, J. Biol. Chem., 267:20547–20550, 1992.
White and Marletta, Biochemistry, 31:6627–6631, 1992.
Wolff et al., J. Biol. Chem., 268:9425–9429, 1993.
Wynn et al., Biochemistry, 33:8962–8968, 1994.
Xie et al., Science, 256:225–228, 1992.

What is claimed is:

1. A method of producing nitric oxide synthase comprising:
   (i) obtaining a protease-deficient prokaryotic cell, the cell comprising a first nucleotide sequence that encodes a nitric oxide synthase, and a second nucleotide sequence that encodes a chaperonin that is in the class of GroEL and GroES;
   (ii) growing the cells in the presence of heme precursor (d-aminolevulinate) or flavin precursors; and
   (iii) isolating nitric oxide synthase from the cell.

2. A method of producing nitric oxide synthase comprising:
   (i) obtaining a protease-deficient prokaryotic cell, the cell comprising a first nucleotide sequence that encodes a nitric oxide synthase, and a second nucleotide sequence that encodes a chaperonin that is in the class of GroEL and GroES;
   (ii) growing the cells in the presence of heme precursor (d-aminolevulinate) and flavin precursors; and
   (iii) isolating nitric oxide synthase apoenzyme from the cell.

3. A method of producing nitric oxide synthase comprising:
   (i) obtaining a protease-deficient prokaryotic cell, the cell comprising a first nucleotide sequence that encodes a nitric oxide synthase, and a second nucleotide sequence that encodes a chaperonin that is in the class of GroEL and GroES;
   (ii) isolating nitric oxide synthase apoenzyme from the cell; and
   (iii) incubating the apoenzyme with a source of tetrahydrobiopterin.

4. A method of producing nitric oxide synthase comprising obtaining apoenzyme and incubating the apoenzyme with tetrahydrobiopterin.

* * * * *

UNITED STATES PATENT AND TRADEMARK OFFICE
CERTIFICATE OF CORRECTION

PATENT NO. : 5,919,682
DATED : July 6, 1999
INVENTOR(S) : Bettie Sue Masters; Linda J. Roman; Essam A. Sheta It is certified that error appears in the above-identified patent and that said Letters Patent is hereby corrected as shown below:

Column 17,
Line 41, after "synthase" insert --apoenzyme--.

Signed and Sealed this

Thirty-first Day of July, 2001

*Attest:*

NICHOLAS P. GODICI
*Attesting Officer*     Acting Director of the United States Patent and Trademark Office